(12) United States Patent
East et al.

(10) Patent No.: US 10,277,568 B2
(45) Date of Patent: Apr. 30, 2019

(54) SECURE PATIENT RECORD TRANSMISSION AND REMOVAL

(71) Applicant: EASTIM Tech, LLC, Delray Beach, FL (US)

(72) Inventors: Steven East, West Palm Beach, FL (US); Thomas Stinson, Tequesta, FL (US)

(73) Assignee: CaringOnDemand, LLC, West Palm Beach, FL (US)

( * ) Notice: Subject to any disclaimer, the term of this patent is extended or adjusted under 35 U.S.C. 154(b) by 199 days.

(21) Appl. No.: 14/953,599

(22) Filed: Nov. 30, 2015

(65) Prior Publication Data

US 2017/0155630 A1    Jun. 1, 2017

(51) Int. Cl.
*H04L 29/06* (2006.01)
*G16H 10/60* (2018.01)
*G06F 19/00* (2018.01)

(52) U.S. Cl.
CPC ........... *H04L 63/08* (2013.01); *G06F 19/00* (2013.01); *G16H 10/60* (2018.01); *H04L 63/107* (2013.01)

(58) Field of Classification Search
CPC ...... H04L 63/08; H04L 63/123; G06F 19/322
USPC .......................................................... 726/4
See application file for complete search history.

(56) References Cited

U.S. PATENT DOCUMENTS

| | | | |
|---|---|---|---|
| 2002/0165733 A1* | 11/2002 | Pulkkinen | G06F 19/321 705/2 |
| 2005/0027995 A1* | 2/2005 | Menschik | G06F 19/321 713/193 |
| 2011/0009707 A1* | 1/2011 | Kaundinya | G06F 19/3418 600/300 |
| 2011/0093287 A1* | 4/2011 | Dicks | A61B 5/0022 705/2 |
| 2012/0060030 A1* | 3/2012 | Lamb | H04L 63/0876 713/166 |
| 2013/0197939 A1* | 8/2013 | Shah | G06Q 50/22 705/3 |
| 2014/0303989 A1* | 10/2014 | Ferguson | G06F 21/6245 705/2 |
| 2015/0019254 A1* | 1/2015 | Ibikunle | G06F 21/6245 705/3 |

(Continued)

*Primary Examiner* — Harunur Rashid
*Assistant Examiner* — Sakinah White Taylor
(74) *Attorney, Agent, or Firm* — Melvin K. Silverman

(57) ABSTRACT

The technology relates to securely providing patient data to caretakers. Verification information from one or more patients may be received by one or more processors. The verification information may include data associated with each of the one or more patient's service locations. The one or more processors may store the patient data for each of the one or more patients in association with the patient's respective verification information. Upon receiving an authentication request including authentication information associated with a caregiver's location, to view a first patient's data, the one or more processors may determine whether the caregiver's authentication information satisfies the first patient's verification information. Upon determining the caregiver's authentication information satisfies the first patient's verification information, controlling the release of the first patient's data to a caregiver's device.

14 Claims, 9 Drawing Sheets

(56) References Cited

U.S. PATENT DOCUMENTS

| | | | |
|---|---|---|---|
| 2015/0254470 A1* | 9/2015 | Glazer | G06F 21/6218 726/27 |
| 2015/0310173 A1* | 10/2015 | Coney | G06F 21/6245 705/3 |
| 2015/0356250 A1* | 12/2015 | Polimeni | G16H 10/60 705/3 |

* cited by examiner

300

400

500

600

# SECURE PATIENT RECORD TRANSMISSION AND REMOVAL

BACKGROUND

With the rise of an on-demand economy consumers have come to expect quick access to goods and services. The healthcare industry has been slow to adapt to the changing economic landscape. As such, healthcare patients are confronted with frustrating consumer experiences while dealing with healthcare service providers, while healthcare service providers have difficultly receiving the information needed to provide the consumers with necessary and expected care. Inconveniences such as long waits at medical offices and not knowing who will be providing the care are just some of the common issues which add to patients' frustrations.

Recently there has been an effort to bring the healthcare industry in line with the demands of the patients. Some such efforts have resulted in allowing patients to schedule appointments online. However, such scheduling systems simply remove a human element from the appointment scheduling process, as patients interact with a website instead of a receptionist or operator. The online scheduling systems continue to fail the needs of today's patients, as patients still continue to face long waits for treatment from caregivers which they know nothing about.

Accordingly, there is a need for systems, apparatuses and methods which provide patients, as well as their caregivers, with the tools necessary to consistently achieve the best healthcare experiences possible.

SUMMARY

Embodiments within the disclosure relate generally to secure patient record transmission and removal. One aspect includes a method for securely providing patient data. Verification information for one or more patients including data associated with each of one or more patient's service may be received by one or more processors. The one or more processors may store the patient data for each of the one or more patients in association with the patient's respective verification information. An authentication request to view a first patient's data, wherein the authentication request includes authentication information associated with a caregiver's location, may be received by the one or more processors. The one or more processors may determine whether the caregiver's authentication information satisfies the first patient's verification information, and upon determining the caregiver's authentication information satisfies the first patient's verification information, controlling release of the first patient's data to a caregiver's device.

Another aspect of the present technology may include a system for securely providing patient data. The system may include a one or more processors and memory storing instructions which executable by the one or more processors. The instructions may include receiving verification information for one or more patients, the verification information including data associated with each of the one or more patient's service locations with the one or more computing devices. The computing devices may store patient data for each of the one or more patients in association with the patient's respective verification information. The one or more computing devices may receive an authentication request to view a first patient's data, wherein the authentication request includes authentication information associated with a caregiver's location and determine whether the caregiver's authentication information satisfies the first patient's verification information. Upon determining the caregiver's authentication information satisfies the first patient's verification information, controlling release of the first patient's data to a caregiver's device.

A further aspect of the present technology may include a non-transitory computer-readable medium storing instructions that when executed securely provide patient data. The instructions cause the one or more processors to perform the steps of receiving verification information for one or more patients, the verification information including data associated with each of the one or more patient's service locations; storing patient data for each of the one or more patients in association with the patient's respective verification information; receiving an authentication request to view a first patient's data, wherein the authentication request includes authentication information associated with a caregiver's location; determining whether the caregiver's authentication information satisfies the first patient's verification information; and upon determining the caregiver's authentication information satisfies the first patient's verification information, controlling release of the first patient's data to a caregiver's device.

BRIEF DESCRIPTION OF THE DRAWINGS

The foregoing aspects, features and advantages of the present invention will be further appreciated when considered with reference to the following description of exemplary embodiments and accompanying drawings, wherein like reference numerals represent like elements. In describing the exemplary embodiments of the invention illustrated in the drawings, specific terminology may be used for the sake of clarity. However, the aspects of the invention are not intended to be limited to the specific terms used.

DETAILED DESCRIPTION

Figure 1:
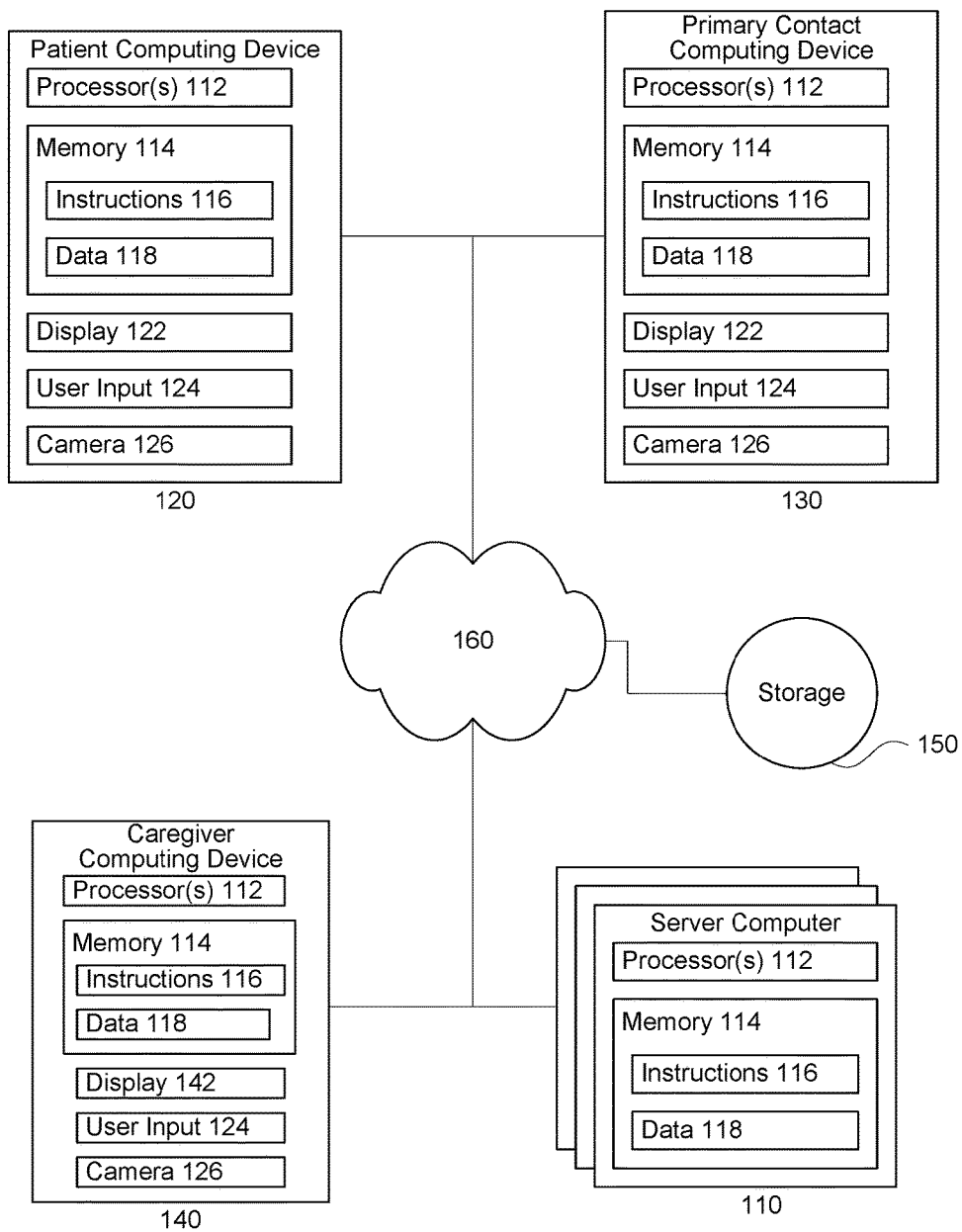
FIG. 1 is a functional diagram of an example system in accordance with aspects of the disclosure.

This technology relates to, by way of example, providing patients with the ability to manage their personal healthcare. In this regard, a healthcare program may be established which provides patients with the ability to determine their level of care needs based on our self-assessment tools, and schedule an appropriate caregiver based on their needs. In addition, the healthcare program may allow caregivers to accept or decline appointments, providing caregivers with the ability to agree to appointments which fit within their schedule and with patients to whom they feel comfortable providing services. By having both the patients and caregivers agree to the appointments, it can be assured that both parties are willing participants to the appointments.

The technology may also manage patient data, including confidential health information, in a manner which assures the data is only viewed by those explicitly granted access. For example, the technology may provide caregivers with access to patient data such as general patient information at the time of appointment scheduling, to allow the caregiver to decide whether or not they would like to take the scheduled appointment. Such general patient information may include the patient's name, address, photo, reason for the scheduled appointment, etc. The technology may also provide secure patient information to the caregiver upon arrival to the scheduled appointment. Such secure patient information may include the patient's health history, prescription history, and other such information which may be covered by legal regulations, such as the Health Insurance Portability and Accountability Act (HIPAA). Upon completion of the scheduled appointment, the secure patient data may then be removed from the caregiver's possession, assuring the patient data remains secure.

The healthcare program may be operated by one or more organizations. In this regard, the organization may be an entity or combination of entities, such as health insurance companies, healthcare providers, doctors, nurses, or one or more natural persons. In certain embodiments multiple healthcare programs may be operated by one or more organizations, with each healthcare program containing its own set of caregivers and/or patients. In some embodiments, a group of caregivers which join the healthcare program may also operate the organization which runs the healthcare program.

The caregivers, who form a network of caregivers within the healthcare program, may include nurses, doctors, and other healthcare providers that are capable of providing healthcare services to patients. The caregivers may join the healthcare program as an employee of the healthcare program, a contractor of the healthcare program, or as an individual caregiver. Every potential caregiver may be subjected to background checks to assure they satisfy certain criteria required by the healthcare program to join as a caregiver. The criteria may include work credentials, past work experience, certain educational degree or background, no criminal record, and other such criteria typically relevant to the hiring of employees.

Individuals may join the healthcare program as patients by signing up in person with a health care representative, online via a healthcare program website, or by calling a health care representative. In some embodiments individuals may only be allowed to sign up for the healthcare program if they meet certain criteria. Such criteria may include age limits, medical history, medical needs, location of residence, etc. In one embodiment primary client contacts may serve as proxies for eligible individuals, and may sign up for the healthcare program on behalf of the eligible individuals. Primary client contacts may include relatives of the patient or persons who have received legal permission to represent the patient as a guardian or otherwise. In this regard, primary client contacts may perform all of the functions and methods as described in relation to the patient.

Upon joining the healthcare program, patients may be presented with a self-assessment questionnaire. The questionnaire may include a number of questions, such as five, or more or less, which may be used to determine the patient's preferences and needs. Based on the results of the self-assessment, a list of available caregivers tailored to the patient's needs, and which may satisfy the patient's preferences, may then be determined. Available caregivers may be tailored to the patient's needs based on the caregiver's skills, preferences, work history, and geographic location. The list of available caregivers may then be presented to the patient for scheduling purposes, described further herein. In some embodiments a home health consultant, who works with new patients as a contractor or employee of the healthcare program, may contact and/or otherwise meet with the new patient and personally present the questionnaire to the new patient.

Location information for each caregiver in the healthcare program may be tracked using location signals from the caregivers' computing devices, such as the caregivers' mobile phones. Based on the tracked location information of the caregivers, real-time scheduling may be provided. For example, patients may be notified when their scheduled caregiver is on the way to an appointment or that the caregiver is going to be late or not make the appointment. In another example, the location information of a backup caregiver may be tracked to assure that a backup caregiver is available should the selected caregiver be unable to make a scheduled appointment.

The features described herein may allow for patients to take full control of their healthcare scheduling and personal healthcare data. Further, patients may be able to select caregivers which are highly rated, and have a track record of providing good care. Caregivers also receive many benefits as they are provided the option to only accept patient appointments with patients they get along with and patients which have needs they can provide for. Caregivers can also accept patients only for times they wish to work. As such caregivers can assure the care a patient needs. Such features remove many of the inconveniences experienced by patients, such as allowing patients to receive care at times and places they desire.

Example Systems

Figure 2:
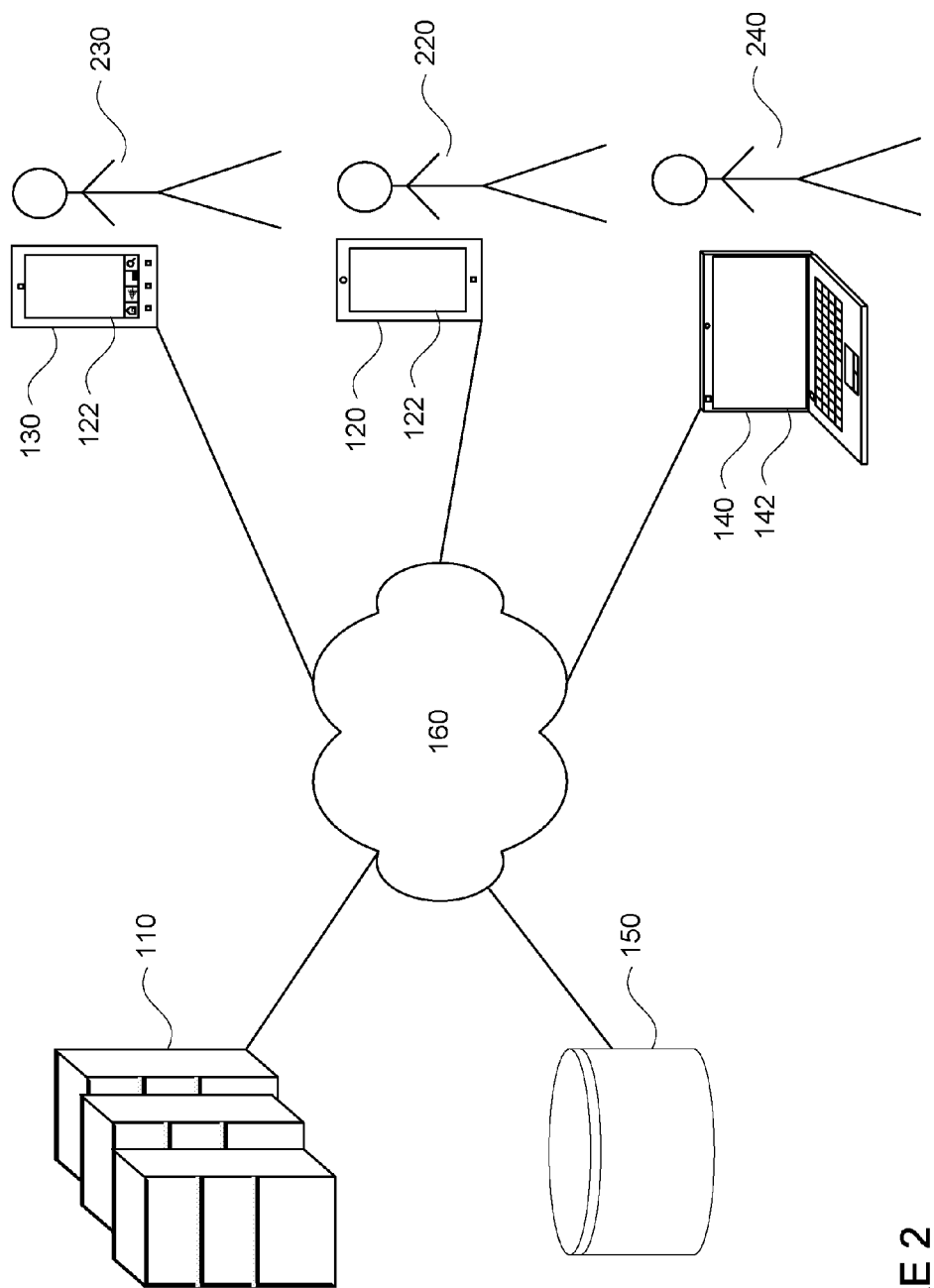
FIG. 2 is a pictorial diagram of the example system of FIG. 1.

FIGS. 1 and 2 include an example system 100 in which the features described herein may be implemented. It should not be considered as limiting the scope of the disclosure or usefulness of the features described herein. Example system 100 may include computing devices 110-140, which include server computer 110, patient computing device 120, primary contact computing device 130, and caregiver computing device 140, as well as storage system 150. Each computing device 110-140 can contain one or more processors 112, one or more memory 114, and other components commonly found in general and special purpose computing devices.

Memory 114 of each of computing devices 110, 120, 130, and 140 can store information accessible by the one or more processors 112, including instructions 116 that can be executed by the one or more processors 112. Memory 114 can also include data 118 that can be retrieved, manipulated or stored by the processor. The memory can be of any type capable of storing information accessible by the processor, such as a hard-drive, memory card, ROM, RAM, DVD, CD-ROM, write-capable, read-only memories, and other such non-transitory types of memory.

Instructions 116 can be any set of instructions which may be executed directly or indirectly by a processor. The instructions may be stored in any format which may be read and executed by the processor. The operations which the instructions cause the one or more processors to execute are explained in more detail below. The terms "instructions,"

"application," "steps," and "programs" can be used interchangeably herein. Data 118 may be read and executed by the one or more processors 112 in accordance with the instructions 116.

Data 118 may be retrieved, stored or modified by the one or more processors 112 in accordance with the instructions 116. For instance, although the subject matter described herein is not limited by any particular data structure, the data can be stored in many types of formats such as, but not limited to, binary values, ASCII or Unicode. Moreover, the data can comprise any information sufficient to identify the relevant information, such as numbers, descriptive text, proprietary codes, pointers, references to data stored in other memories such as at other network locations, or information that is used by a function to calculate the relevant data.

The one or more processors 112 can be any conventional processors, such as commercially available CPUs from Intel, AMD, or Apple. Alternatively, the processors can be dedicated components such as an application specific integrated circuit ("ASIC") or other hardware-based processors, such as ARM processors or System on Chips (SoCs). In addition to CPUs, processors 112 may include other processors such as GPUs from AMD or NVIDIA.

Although FIG. 1 functionally illustrates the processor, memory, and other elements of computing device 110 as being single components, the processor, computer, computing device, or memory can actually comprise multiple processors, computers, computing devices, or memories that may or may not be positioned within the same physical housing. For example, the memory can be a hard drive or other storage media located in housings different from that of the computing device 110. The same may be true of the other computing devices 120-140. Accordingly, references to a processor, computer, computing device, or memory will be understood to include references to a collection of processors, computers, computing devices, or memories that may operate in series or in parallel. Further, although some functions described below are indicated as taking place on a single computing device having a single processor, various aspects of the subject matter described herein can be implemented by a plurality of computing devices.

Each computing device 110-140 may also be implemented by directly and indirectly communicating over a network 160. In this regard, each of the computing devices 110, 120, 130, and 140 can be at different nodes of a network 160 and capable of directly and indirectly communicating with other nodes of network 160. While only four computing devices 110-140 are shown in FIGS. 1-2, it should be understood that a system may include a large number of computing devices, each at different nodes of the network 160. For example, each patient may have at least one patient computing device 120, and each caregiver would typically have at least one caregiver computing device 140.

The network 160 and intervening nodes described herein can be interconnected using various protocols and systems. For example, the network 160 may be implemented via the Internet, intranets, local area networks (LAN), wide area networks (WAN), etc. Communication protocols such as Ethernet, WiFi, and HTTP, Bluetooth, LTE, 3G, 4G, Edge, etc., and various combinations of the foregoing.

As an example, each of the computing devices 110-140 may include web servers capable of communicating with storage system 150 via the network. For example, one or more of server computing devices 110 may use network 160 to transmit and present information to a user, such as patient 220, primary contact 230, or caregiver 240, on a display, such as displays 122 or 142 of computing devices 120-140.

Each computing device 120, 130, or 140 may be a personal computing device intended for use by a user 220, 230, 240, and have all of the components normally used in connection with a personal computing device such as a central processing unit (CPU), graphical processing unit (GPU), memory (e.g., RAM, ROM, SSD, HD, etc.) storing data and instructions, a display such as displays 122, 132, or 142, and user input device 124. The computing devices 110-140 may also include a camera for recording/capturing video streams and/or capturing images, speakers, a network interface device, and all of the components used for connecting these elements to one another. Each computing device 110-140 may perform all or some of the features described herein.

Although the client computing devices 120, 130, and 140 may each comprise a full-sized personal computing device, they may alternatively comprise mobile computing devices capable of wirelessly exchanging data with a server computer 110 over a network such as the Internet. By way of example only, patient computing device 120 may be a mobile phone or a device such as a PDA, a tablet PC, or a netbook that is capable of obtaining information via the Internet.

The patient computing device 120 may be configured to provide specific functions in accordance with embodiments of the technology. For example, the patient computing device 120 may be programmed to allow the patient to schedule caregivers, set up their personal accounts, manage their payment information such as storing credit card information, receive real-time information on caregiver locations, allow for daily feedback for services rendered, and create customized care requests and assignments for the caregivers. Additionally the patient computing device 120 may be configured to allow the patient to sign-up for the healthcare program, view their daily schedule, and view past appointment statements.

Patient computing device 120 may also be configured for use as a home base. For example, the patient computing device 120 may be programmed to run only a healthcare program patient application which is capable of performing the methods described herein. In some embodiments the home base may be programmed to limit the patient computing device to perform only the specific functions described herein, thereby limiting the functionality of the computing device. While the home base is described as being implemented on the patient computing device 120, it should be understood that any of the computing devices may be configured as a home base. Further, the home base may also be implemented on other hardware, such as a network switch, router, network attached storage device, or even implemented as a stand-alone unit. Such other implementations may include some or all of the features of the home base as described herein. In some embodiments the home base may be provided by the healthcare program. Alternatively, the patient computing device 120 may already belong to the patient, and as such, may programmed to operate as a home base. The terms home base and patient computing device 120 may be used interchangeably, as they may be capable of performing the same functions and methods. In some embodiments the functions of the home base and patient computing device 120 may be different.

The home base may be programmed to switch into an idle mode while not in use. Idle mode may result in the home base functioning as a digital photo album, a video player, a music player, or other such multimedia player. For example, the home base may play a slide show of stock photos or of a patient's own photos after a period of inactivity. In this regard the home base may store a local collection of the patient's photos. Alternatively, or in addition to a local collection of the patient's photos, the home base may display images which are from a patient's social media account or otherwise stored remotely from the home base, such as on an external web serve.

The home base may also be configured to provide stimulation to a patient. For example, the home base may be programmed to wake up a patient at a predetermined time with specific sounds. In one example, the home base may play the sound of birds while waking a patient who suffers from dementia. In another example, the home base may play the patient's favorite song, playlist, or radio station. Such media may be stored within the home base and/or or remotely from the home base.

In further embodiments, the home base may also display a calendar of the patient's schedule. For example, the home base may display, at predetermined time periods, such as in the morning, every hour, every few minutes, etc., the patient's hourly, daily, weekly, monthly, etc., schedule. In some embodiments the calendar may be displayed only during daytime hours. In one embodiment, the home base may be programmed to display the caregiver's photo and profile information at the time of or near a scheduled appointment.

In other embodiments, the home base may also allow for social networking by the patient. For example, the home base may present to the patient local groups that the client may or may not be interested in attending. Such groups may be based on the patient's selected hobbies and interests. The patient may also request a meeting or "Meet Up" should one of the local groups be of interest to the patient. These events and requests may be presented on the home base, where the client may be able to accept or reject the events and requests.

In some embodiments, the primary contact computing device 120 may be programmed to perform all of the functions of the home base. Further, the primary contact computing device 130 may also be programmed to perform all of the functions of the patient client computing device 120.

Caregiver computing device 140 may be configured to provide specific functions in accordance with embodiments of the technology. In some embodiments the caregiver device may be programmed to execute a mobile caregiver application. The mobile caregiver application may be able to perform all of the methods described herein. In some embodiments the caregiver application may limit the caregiver's computing device 140 to perform only the specific functions described herein, thereby removing functionality of the computing device. In some embodiments the caregiver computing device 140 may be programmed to perform all of the functions of the patient computing device 120 and further the ability to publish a profile and further profile extensions, such as badges, adding new work experience or new education accomplishments.

The caregiver device 140 may be configured to monitor health metrics. For example, the caregiver device 140 may be configured to monitor a patient's basic health vital signs through wireless and wired peripherals, such as heart rate monitors, blood oxygen sensors, EKGs, ECGs, etc. The measured vital signs may be sent to a central server, such as the server computer 110, for storage in association with the respective patient's data.

Storage device 150 can be of any type of storage capable of storing information accessible by the server computing devices 110, member computing device 120, or retail computing device 140, such as a hard-drive, a solid state hard drive, NAND memory, ROM, RAM, DVD, CD-ROM, write-capable, and read-only memories. In addition, storage device 150 may include a distributed storage device where data is stored on a plurality of different storage devices which may be physically located at the same or different geographic locations, such as network attached storage. Storage device 150 may be connected to the computing devices via the network 160 as shown in FIG. 1 and/or may be directly connected to any of the computing devices 110, 120, and 140.

An organization may operate one or more central servers which maintain patient data for each patient who signs up for the healthcare program. In this regard, the central server, such as server computer 110, may maintain one or more storage devices which store the patient data, as well as patient preference data for each patient of the healthcare program in a database. In some embodiments, one or more of the functions of the central servers, such as server computer 110, may be implemented by any one of computing devices 120-140. As such, the patient and/or caregiver may operate servers which perform the functions of the server computer 110 in place of, or in concert with the organization's central server.

The storage devices, such as storage device 150 may store, for each patient, patient data in a database. In some embodiments, one or more of the functions of the central servers, such as server computer 110, may be implemented by the patient computing device 120. As such, the patient may operate the servers or patient computing devices which perform the functions of the server computer 110 in place of, or in concert with the organization.

The central server may store patient data. As previously described, the patient data may include secure health information and general patient information, as well as patient preferences. Secure health information may include data such as patient's health history, prescription history, patient medical diagnosis, patient treatment history, and other such information which may be covered by HIPAA regulations. General patient information may include the patient's name, address, date of birth, age, sex, phone number, email address, patient's photo, reasons for the scheduled appointments, etc. Patient preferences may include desired caregiver traits, such as the caregiver's skills, attributes, work history, work experience, and geographic location. In one embodiment patient preferences may also include a list of backup caregivers which were approved by the patient to provide services should their selected caregiver be unable to attend an appointment. Patient preferences may also include an indication of whether or not the healthcare program should always send a caregiver, even if the selected caregiver and selected backup caregivers are unavailable. Patient preferences may further include an indication of an acceptable time window for which a selected caregiver may arrive, such as 15 minutes before or after a scheduled start time of an appointment. In some embodiments the patient data may be stored on the respective patient's and/or primary's client computing device.

In some embodiments the central server may store patient verification information for each patient. In this regard, patient verification information may include data associated with each of the one or more patient's service locations. In some embodiments the patient verification information may include at least one of a validation token, a geolocation for each of the one or more patient's service locations, a geotagged location (i.e., a hospital where the patient is receiving treatment), or networking data for each of the one or more patient's service locations. Such patient verification information for each patient may be stored in association with each respective patient's data.

The central server may also store caregiver profiles. Caregiver profiles may include any or all of the caregiver's name, address, date of birth, age, sex, contact information including a phone number and email address, caregiver's photo, caregiver videos, educational experience, work experience, skills, ratings, reviews, and accolades. The caregiver profiles may also be stored directly on each respective caregiver's computing devices 140. Such caregiver profiles may be accessible by the patients and primary contacts.

In some embodiments, caregiver profiles will include a cumulative report based on caregiver professional experience, skills and attributes. Caregiver skills may be determined based on a standardized testing process for each skill or work history. For each skills test a caregiver scores above a predetermined threshold score, a skills badge may be earned and added to the caregiver's profile. A skill may also be determined based on whether the caregiver has provided care for a certain type of treatment, such as Alzheimer's or dementia. In some embodiments, the home base may be configured to display the caregiver's profile information, including the caregiver's picture during or at a predetermined time before a scheduled appointment. By doing so the patient may be assured that the caregiver who arrives to the scheduled appointment is the selected caregiver whom they expected.

The central server may also store the location information of each caregiver. In this regard, the location signals and information, such as GPS signals indicating a caregiver's geographical location, for each caregiver may be transmitted from each caregiver's computing device, such as device 140, to the central server, such as the server computer 110. The central server may then store the received location information of each member in association with each caregiver. The central server may store the location information in the same, or a different, database as the patient data. In some embodiments the central server may receive real-time location information from each caregiver's computing device 140. In addition, the location information may include historical geolocation information indicating locations each caregiver previously traversed, patients which were visited, etc.

Example Methods

For purposes of highlighting features of the present invention, exemplary processes for managing the scheduling of appointments and release of patient data as shown in FIGS. 3-8, are described below in connection with operations performed at components of the system 100, as described in FIGS. 1 and 2. It is to be understood that the some or all of the operations performed at the patient computing device 120 may be performed at the primary contact computing device 130, and some or all of the operations performed at the patient computing device 120 may be performed at the server computer 110 or caregiver computing device 140. Additionally, some or all of the operations performed at the caregiver computing device 140 may be performed at the server computer 110.

Figure 3:
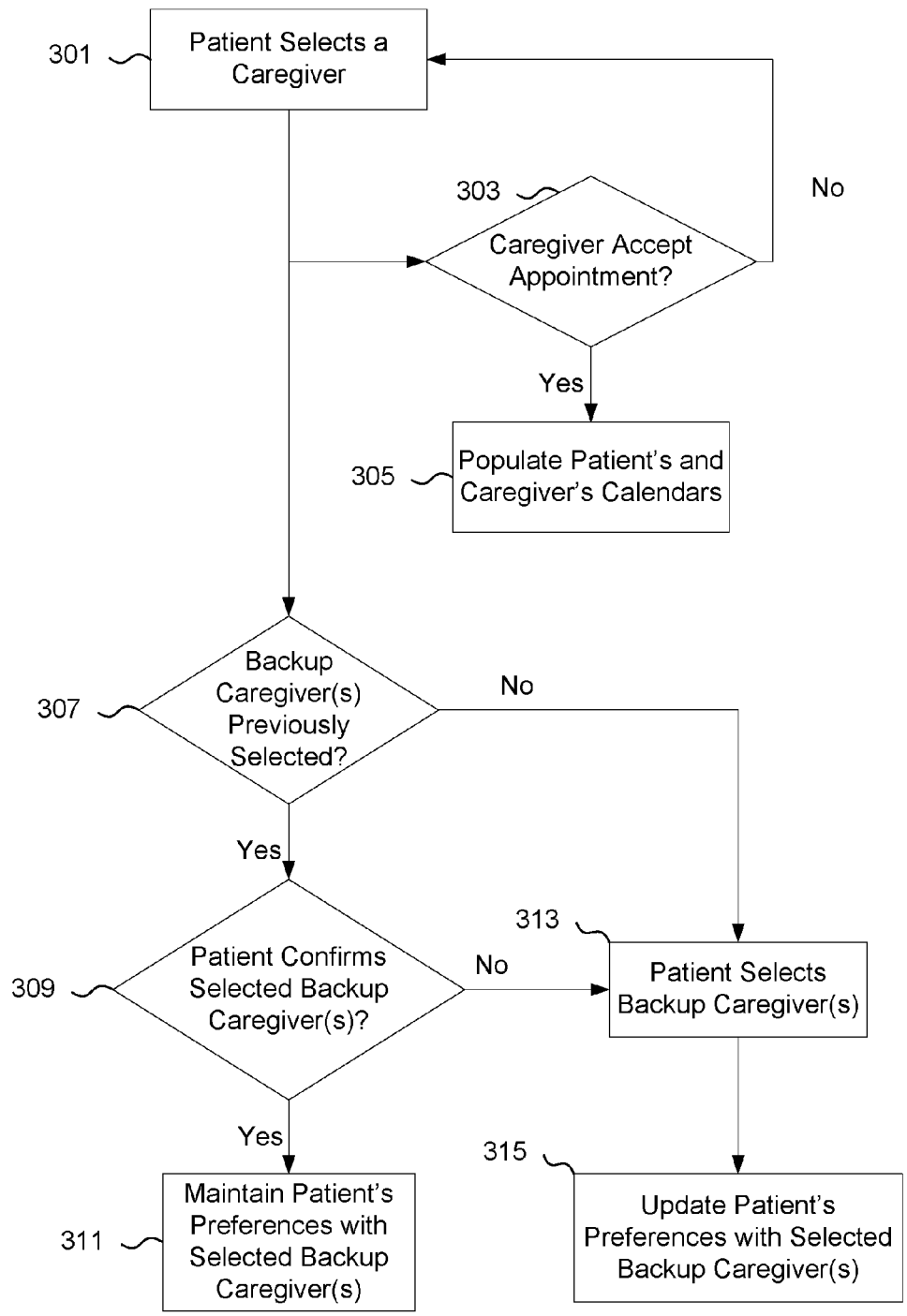
FIG. 3 is a flow diagram of scheduling a caregiver for an appointment in accordance with embodiments of the disclosure.

Referring now to FIG. 3, a patient who has joined the healthcare program, as previously described, may schedule an appointment as shown in diagram 300. In this regard, within the healthcare program patient application a list of the available caregivers may be presented to the patient on the display of a computing device, such as display 122 of patient computing device 120. The available caregivers may be presented in an order based on the patient's profile, patient's health information, and caregiver's profile. In some embodiments the order of available caregivers presented to the patient may be based on the caregivers' ratings.

As show in block 301, the patient may select a caregiver from the network of available caregivers belonging to the healthcare program. Upon selecting a caregiver for an appointment, the device 120 may communicate via network 160 with the caregiver computing device 140, or the server computer 110 which is in turn may communicate with the caregiver computing device 140 via the network 160, such that the selected caregiver may be notified in the mobile caregiver application on their caregiver computing device 140, that a patient has requested their services. Further information may also be provided to the selected caregiver such as the patient's general patient information, including the patient's name, address, photo, reasons for the scheduled appointments, and other such patient information as previously described. Further, the selected caregiver may be provided with the patient's preferences. In this regard the general patient information and patient preferences may be sent from the central server, such as the server computer 110, and/or directly from the patient's computing device.

The selected caregiver may be given the opportunity to accept or decline the appointment, as shown in block 303. In this regard, the selected caretaker may evaluate the patient's general information and preferences. Should the selected caregiver decline the appointment, the patient may be asked to select a different caretaker as shown in block 301. In some embodiments, should the selected caregiver decline the appointment, the system may automatically assign an available backup caregiver as a selected caregiver.

Should the selected caregiver accept the appointment, the patient's and caregiver's schedules and calendars will be populated with the appointment details, as shown in block 305. For example, the calendar stored on the patient's computing device 120 may be updated with the information of the scheduled appointment. Additionally, the selected caregiver's schedule and calendar, stored on the central server, such as the server computer 110, and/or caregiver's computing device 140, may be updated to include the information of the schedule appointment. The information of the scheduled appointment may include the date, time, and location of the appointment, as well as the purpose of the appointment, the selected caregiver's name, and the patient's name.

As further shown in FIG. 3, upon selecting a caregiver, the healthcare program patient application may determine if the patient's preferences include previously selected backup caregivers, as shown in block 307. For example, the patient's computing device may query the central server, to determine if the patient's preferences include any previously selected backup caregivers. In the event the patient's preferences include previously selected backup caregivers, the patient may be prompted to confirm a desire to have the previously selected backup caregivers remain as selected backup caregivers, as shown in block 309. Upon confirmation of the previously selected backup caregivers, the patient's preferences may be maintained with the selected backup caregivers, as shown in block 311.

Turning now to block 313, in the event the patient has not previously selected backup caregivers, or if the patient does not confirm the previously selected backup caregivers, the patient may be prompted to select backup caregivers for the appointment. For example, the healthcare program patient application may present a list of the available backup caregivers to the patient on the display of the patient computing device 120, as shown in block 313. The list of available backup caregivers may be determined from the network of available caregivers which satisfy the patient's preferences, as previously described. In some embodiments the patient may select one or more backup caregivers, or no backup caregivers. Upon selecting backup caregivers, the patient's preferences may be updated with the selected backup caregivers, as shown in block 315.

Figure 4A:
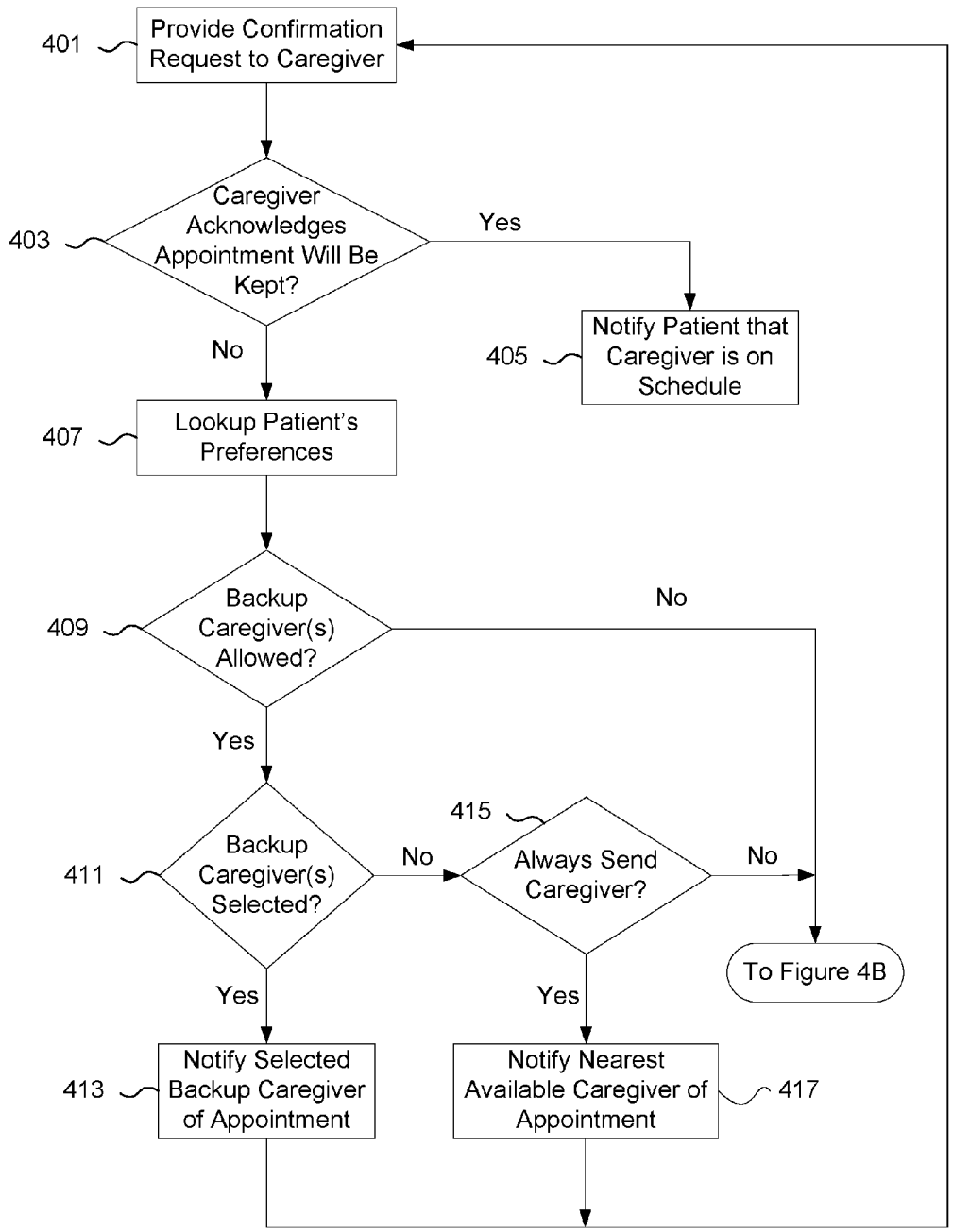
FIG. 4A is a flow diagram of confirming a caregiver will make a scheduled appointment in accordance with aspects of the disclosure.

Referring now to FIG. 4A, the patient and scheduled caregiver may receive notifications and inquiries regarding upcoming scheduled appointments, as shown in flow diagram 400. For example, as the scheduled appointment draws closer in time a confirmation request may be presented at the caregiver's computing device 140, as shown in block 401. The confirmation request may require the selected caregiver for an appointment to indicate whether they will be able to make the appointment or not. The confirmation request may be provided from the server computer 110 or from the mobile caregiver application executing on the caregivers computing device 140. In some embodiments the confirmation request may be automatically generated based on a predetermined time period before an appointment, such as thirty minutes, or more or less. The confirmation request may be provided through an Interactive Voice Recording (IVR), an SMS, an email, and/or a push notification.

In some embodiments the confirmation request may be generated based on the geolocation of the selected caregiver. For example, based on the geolocation of the selected caregiver, determined by the caregiver's location signal, the time it would take for the selected caregiver to reach a scheduled appointment may be determined. The confirmation request may then be generated based on the determined time it would take for the selected caregiver to reach the appointment. In one example, if it is determined it would take the selected caregiver thirty minutes to reach a scheduled appointment a confirmation request may be generated forty minutes, or more or less, before the scheduled appointment. The time it would take for the selected caregiver to reach the appointment may be based on the selected caregiver's location as well as mode of transportation (i.e., car, train, bus, etc.) In one example, the system may account for real-time traffic data to determine the amount of time it would take a selected caregiver to reach a scheduled appointment when the selected caregiver indicates he will be driving to the next appointment via bus, taxi, personal car, etc.

In another embodiment, the confirmation request may be generated based on the location of the backup selected caregiver. For example, based on the geolocation of one or more of the selected backup caregivers, determined from the one or more selected backup caregiver's respective location signals, the time it would take for the selected backup caregivers to reach a scheduled appointment may be determined. The confirmation request may then be generated based on the determined time it would take for one or more of the selected backup caregivers to reach the appointment. In one example, if it is determined it would take a first selected backup caregiver thirty minutes to reach a scheduled appointment a confirmation request may be generated forty minutes, or more or less, before the scheduled appointment. In another embodiment the confirmation request may be generated based on the longest or shortest time it would take one of the selected backup caregivers to reach the scheduled appointment. As such, the healthcare program may be able to assure that the selected caregiver or a backup caregiver is available to make the scheduled appointment. In other embodiments the confirmation request may be generated based on the location of an on call caregiver, should the patient not have any selected backup caregivers or if the patient's medical condition necessitates or otherwise recommends making sure a caregiver shows for most appointments.

The selected caregiver may then respond to the confirmation request, as shown in block 403. In the event that the selected caregiver acknowledges that the appointment will be kept, a notification may be sent to the patient informing them that the selected caregiver will keep the appointment as shown in block 405. In some embodiments the notification may include the selected caregiver's name, the caregiver's photo, anticipated arrival time, etc.

In the event the selected caregiver acknowledges that the appointment will not be kept, or fails to respond to the confirmation request within a predetermined period of time, alternate arrangements may be made. For example, as shown in blocks 407 and 409, respectively, the patient's preferences, which are stored in a memory, may be reviewed to determine if backup caregivers are allowed. Should backup caregivers not be allowed, the method may proceed to FIG. 4B, as described below.

In some embodiments, the selected caregiver may indicate that he will be late for an appointment, or the server, such as server computer 110 may monitor the selected caregiver's location and determine that the selected caregiver will be late. The patient's preferences may then be reviewed to determine whether the selected caregiver is within the patient's acceptable time window. If the selected caregiver is within the acceptable time window, the flow may proceed to block 405. In the event that the selected caregiver is not within the acceptable time window, the flow may proceed as if the selected caregiver did not acknowledge the appointment will be kept, and proceed to block 409. In the event the selected caregiver may be early for an appointment, the patient's preferences may be reviewed to determine whether the patient's time window allow for early appointments based on the time the selected caregiver is estimated to arrive. In the event the selected caregiver is estimated to arrive prior to the time allowed by the patient's time window, the selected caregiver may not proceed to the appointment, or the selected caregiver may be provided the option to call the patient or patient's primary contact.

Should the patient's preferences allow for backup caregivers, the patient's preferences will be further reviewed to determine if any backup caregivers were selected for the appointment, as shown in block 411. In the event that backup caregivers were selected, an available selected backup caregiver may be notified of the appointment, as shown in block 413. The selected backup caregiver may also receive a confirmation request, as previously described. In this regard, the method steps previously described may be reiterated with regard to the selected backup caregiver. In some embodiments, the backup caregivers may be ranked by the patient, and the highest ranked backup caregiver may be selected, until an available backup caregiver is found.

In the event that no backup caregivers are available, or if the patient has not selected any backup caregivers, the method may proceed to block 415. As shown in block 415, the patient's preferences may be reviewed to determine if the patient always requires a caregiver. If so, the nearest available caregiver will be selected for notified of the appointment, as shown in block 417. In some embodiments, the highest ranked available caregiver may be selected and notified of the appointment. The selected available caregiver may also receive a confirmation request, as previously described with regard to the selected caregiver in block 401. In this regard, the method steps previously described may be reiterated with regard to the selected available caregiver. In the event that no backup caregivers are selected and the patient does not wish to always have a caregiver sent, the method may proceed to FIG. 4B.

Figure 4B:
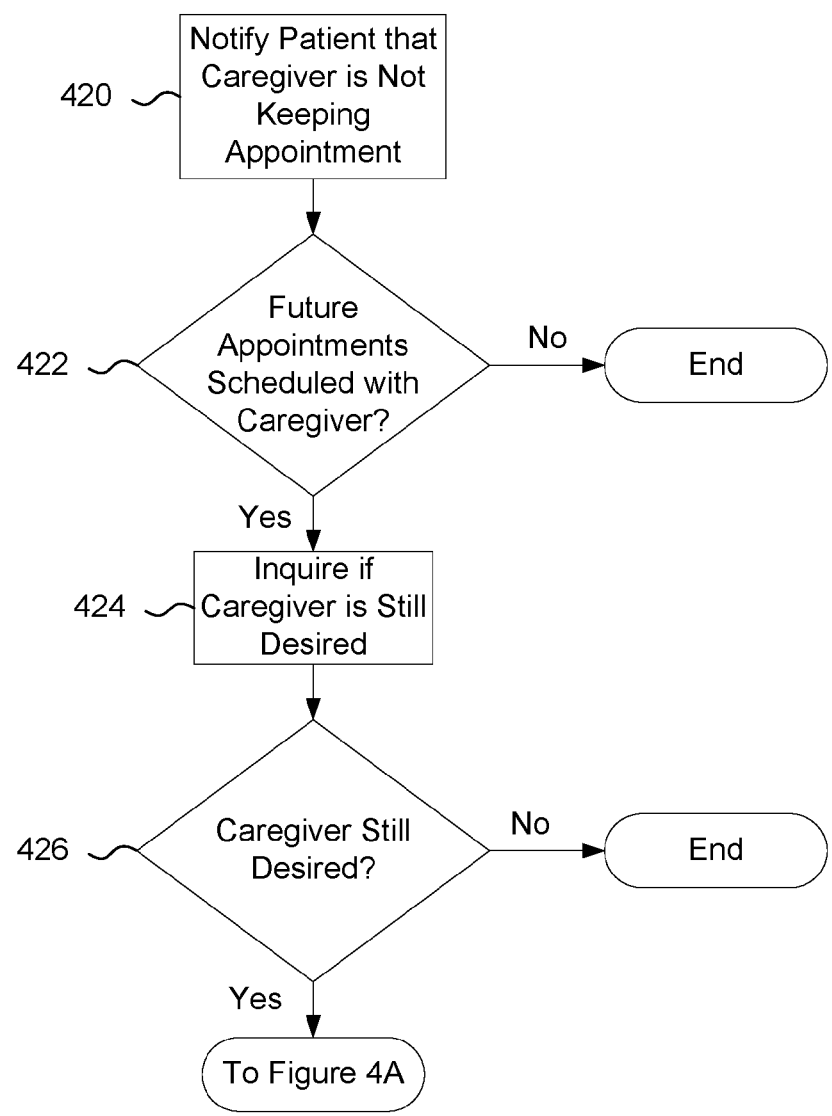
FIG. 4B is a flow diagram of determining whether a patient desires to continue using a caregiver who did not make a scheduled appointment according to one embodiment of the disclosure.

As shown in the flow diagram 400, of FIG. 4B, upon determining that no caregivers are available for an appointment, the patient may be notified. For example, a notification through an IVR, an SMS, an email, and/or a push notification, may be provided to the patient on the patient's computing device 120, as shown in block 420. The notification may include information such as the scheduled appointment time, the selected caregiver's name that was unable to make the appointment and the reason the selected caregiver was unable to make the appointment.

Should the selected caregiver not be able to keep the scheduled appointment, the patient's calendar and/or schedule may be reviewed to determine if the selected caregiver is scheduled for future appointments, as shown in block 422. If the selected caregiver is not scheduled, no further actions may be necessary. Otherwise, an inquiry may be sent to the patient to determine if the patient would still like to work with the selected caregiver as shown in block 424. In the event the caregiver is still desired by the patient, the method may proceed back to FIG. 4A, block 401, else no further actions may be necessary. In some embodiments the inquiry may be sent after the selected caregiver misses a predetermined number of appointments. In other embodiments no inquiry may be sent to the patient if the patient's preferences request not to be asked about continuing to use the selected caregiver.

Figure 5:
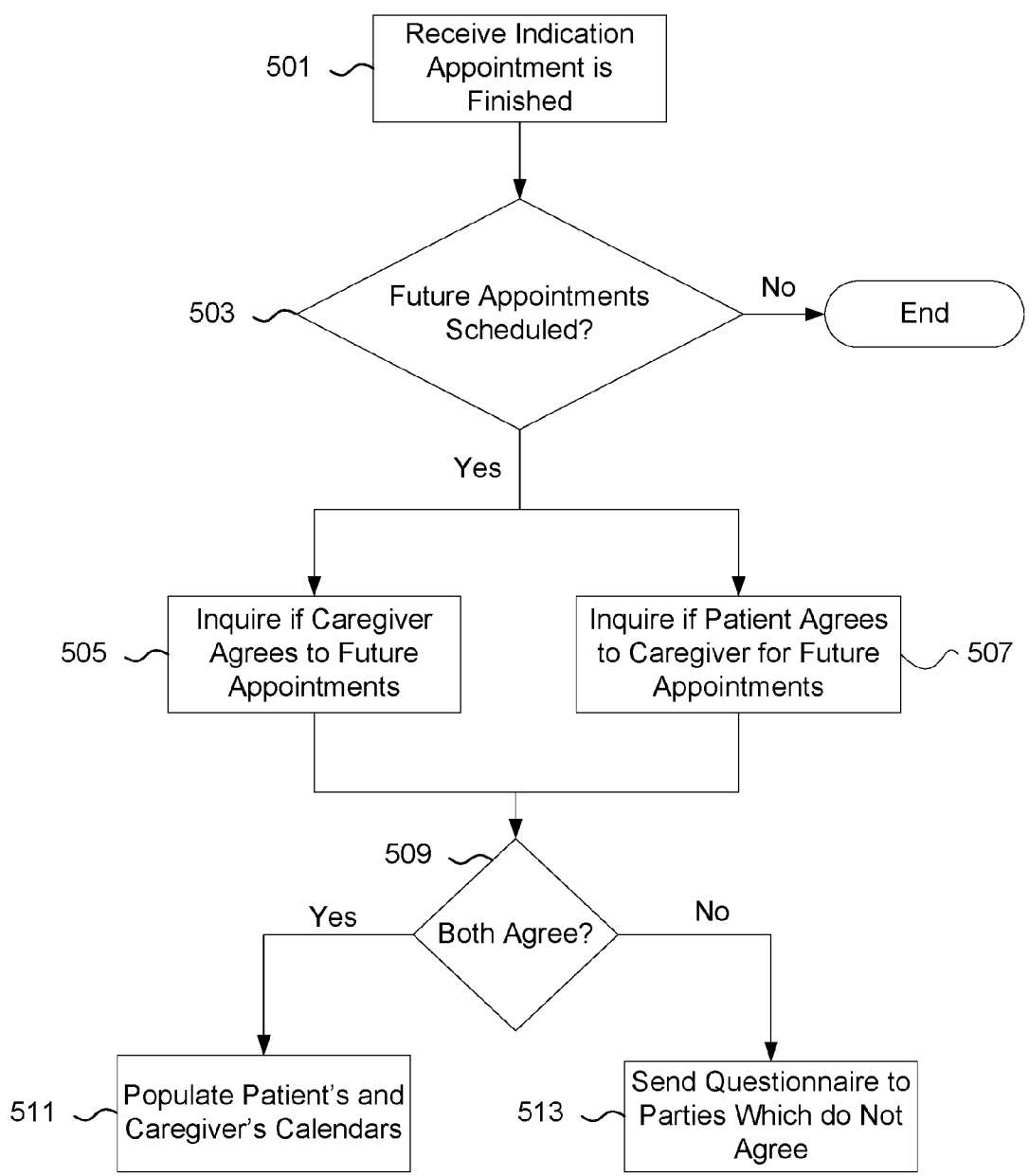
FIG. 5 is a flow diagram of determining whether a patient and caregiver want to continue meeting for future appointments in accordance with the disclosure.

Turning now to FIG. 5, upon completion of a scheduled meeting the selected caregiver and patient may agree to continue their relationship for future appointments, as shown in flow diagram 500. As shown in block 501 an indication may be received by the central server, that the scheduled appointment has been completed. In some embodiments, the selected caregiver, primary client contact, or patient may send a signal from the device 140, 130, or 120, respectively, indicating the scheduled appointment was completed. In other embodiments the central server may monitor the location of the selected caregiver to determine if the selected caregiver has completed the scheduled appointment. For example, the central server may continually monitor the geolocation of the selected caregiver, and determine that the geolocation of the selected caregiver matches the geolocation of the scheduled appointment. As such, the central server may determine the scheduled appointment is in progress. Once the scheduled appointment is determined to be in progress, the central server, such as the server computer 110, may then monitor the caregiver's geolocation for movement away from the geolocation of the scheduled appointment. If the central server determines the location of the caregiver is outside a predetermined vicinity of or greater than a predetermined distance from the scheduled appointment location, a signal may be generated indicating the scheduled appointment was completed.

Although not shown, during a scheduled appointment video and audio feeds of the appointment may be sent to the primary care client's device. As such the client may monitor the scheduled appointment while not needing to be present. The video and audio feeds may include text and hypertext communication abilities. The video and audio feeds may be a one-to-one interchange, one-to-many interchange, many-to-one, or many-to-many interchanges. The type of interchange may be based on the number of caregiver's present for the scheduled appointment and the number of primary care clients.

In some embodiments, by way of example, if a client has a particular diagnosis, such as Congestive Heart Failure (CHF), he will be presented with standard CHF assessment tools as well as the recommended homecare treatment protocol for those who have CHF. When the medications given by the caregiver are logged by the caregiver, patient, or primary contact, the system may analyze the medications and ensure there are medications logged that address CHF. If not a report/alert will be generated to the client and or primary contact and if directed, the client's primary care physician.

Once the scheduled appoint is finished, the method may proceed to block 503, where the central server may determine if future appointments are scheduled between the selected caregiver and the patient. If no future appointments are scheduled no further actions may be necessary. Although not shown, if no future appointments are scheduled, questionnaires may be provided to the patient and selected caregiver requesting each party to review and rate their respective experiences.

When future appointments are scheduled, the caregiver and/or the patient may receive an inquiry to determine if they agree to join the future scheduled appointments, as shown in block 505. Based on the caregiver and patient responses, a determination may be made if both agree or disagree as shown in block 509. If both the parties agree to join the future scheduled appointments, both the patient's and caregiver's respective calendars and schedules may be populated with the future appointments as shown in block 511. Otherwise, the party or parties which do not agree to the future appointment may be provided a questionnaire requesting the parties to review and rate their respective experiences, and further to provide reason why they turned down the future appointments as shown in block 513.

In some embodiments, upon completion of an appointment, patients may be asked to provide feedback on the selected caregiver. Such feedback may be overall job performance Based on the feedback, overall job performance, and specialized skills of the caregiver, along with other such metrics, ratings may be assigned and/or updated to the caregiver. The ratings may be determined based on a weighted average of each metric.

Figure 6:
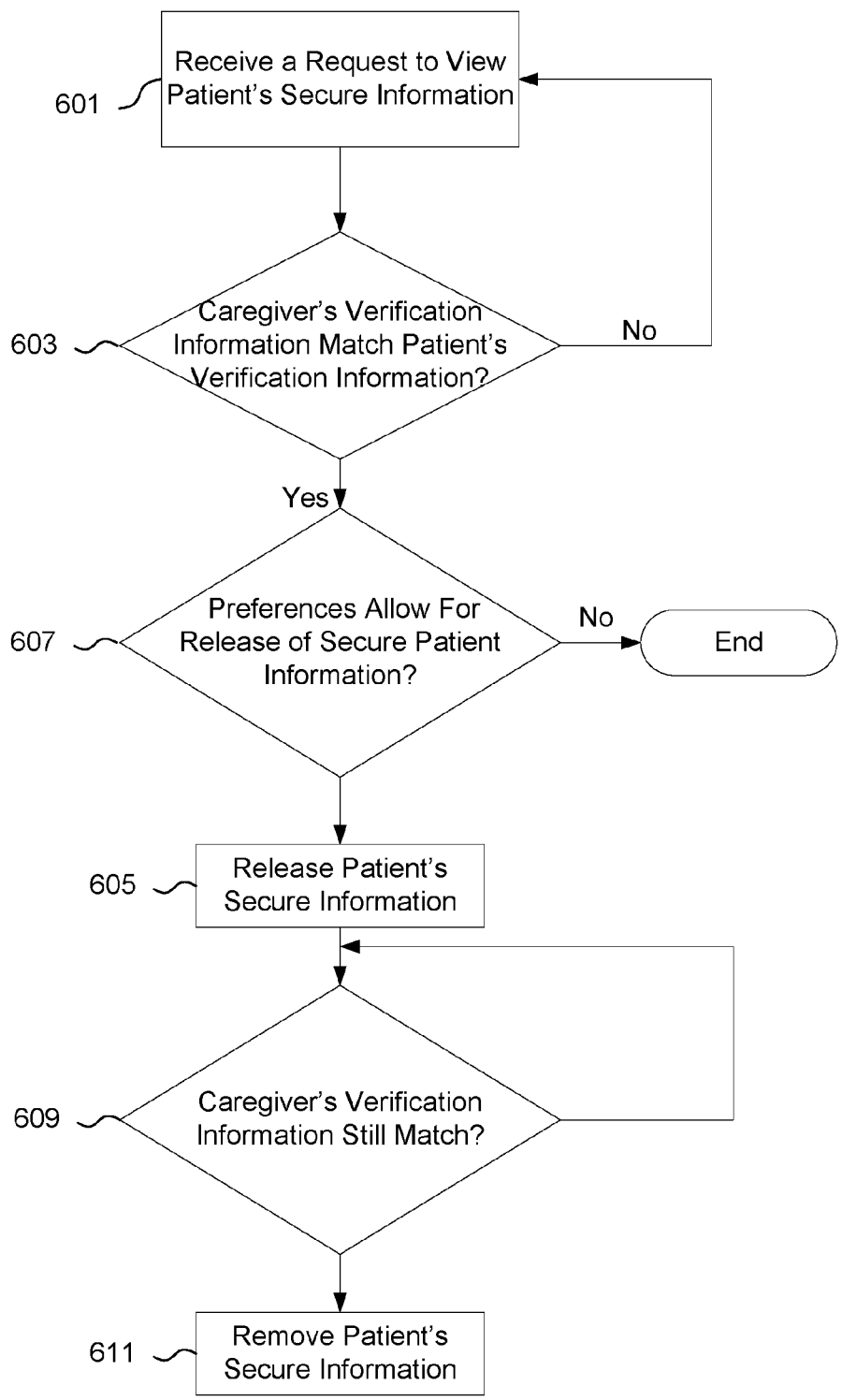
FIG. 6 is a flow diagram of electronic document management in accordance with an aspect of the disclosure.

Turning now to FIG. 6, a flow diagram 600 is shown for securely delivering and removing secure patient information to a scheduled caregiver at a scheduled appointment. As previously described, secure patient information may include the patient's health history, prescription history, and other such information which may be covered by HIPAA regulations. As previously described, verification information may be stored in association with the patient's data, and may be associated with the patient's service locations (i.e., where the patient's appointment is scheduled). In some embodiments the patient's verification information may include geolocation for the patient's service location, networking data for the one patient's service locations, and/or a security token.

Turning first to step 601, the scheduled caregiver's computing device may provide an authorization request to gain access to the patient's secure information. The authorization request may include authentication information associated with a caregiver's location, such as the selected caregiver's geolocation or information on the network to which the caregiver's computing device 140 is connected. In some embodiments the authorization request may be provided automatically by the caregiver's computing device or the central server, or manually requested by the caregiver. In further embodiments, the authorization request may be for one or more patient's secure information, in the event the patient is receiving care at the same location, such as a geotagged location.

Figure 7:
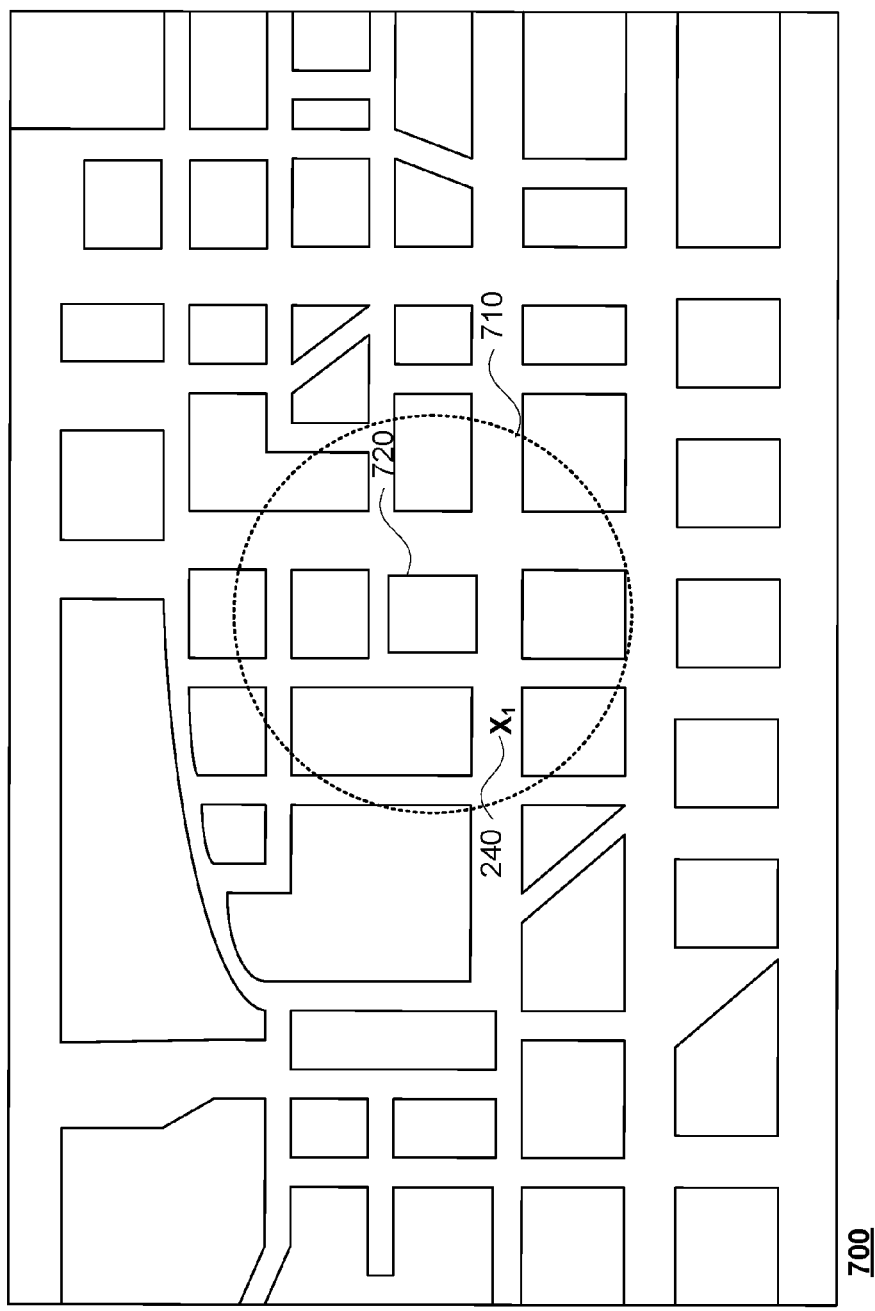
FIG. 7 is an example of caretaker tracking in accordance with one embodiment of the disclosure.

In some embodiments the remote central server, such as server computer 110, may monitor the location of the selected caregiver to determine if they are close to the geolocation of their next scheduled appointment or appointments. Upon determining the selected caregiver is within a predetermined proximity of the patient's service location, such as 50 yards, or more or less, an automatic authorization request may be initiated. For example, as shown in FIG. 7, a selected caregiver 240 may be walking to a scheduled appointment at a patient's service location 720, in neighborhood 700. The central server, may continually monitor the geolocation of the selected caregiver, and determine that the geolocation of the selected caregiver, position X1, is within a predetermined area 710 of the patient's service location 720. Upon determining the caregiver is within the predetermined area 710, the central server may trigger an authorization request on behalf of the caregiver.

In some embodiments the authorization request may be triggered based on geotagged location information. For example, the remote central server, such as server computer 110, may monitor the location of the selected caregiver to determine if the caregiver is close to the geotagged location of his next scheduled appointment or appointments. Upon determining the selected caregiver is within a predetermined proximity of the patient's geotagged location, an authorization request may be initiated. When the selected caregiver has multiple appointments at the same geotagged location, the authorization request may be to view or receive the secure patient data at the caregiver's device for each of the appointments at the geotagged location. In other embodiments the selected caregiver may only be authorized to view a single patient's secure patient data at a time.

In another embodiment the authorization request may be triggered based on time data, such as the time the appointment was scheduled. For example, the central server, such as the server computer 110, or caregiver's device 140 may determine that an appointment is scheduled to occur within a predetermined period of time, such as ten minutes or more or less. Based on the determination that the scheduled appointment is set to occur within the predetermined time period, an authorization request to view or receive the secure patient data at the caregiver's device may be generated.

Turning now to step 603, the caregiver's verification information may be compared to the patient's verification information. If the patient's verification information matches the caregiver's verification information, the secure patient data may be released to the caregiver. In one embodiment, the patient and scheduled caregiver may each be assigned validation tokens. When the caregiver's validation token matches or is otherwise approved by the patient's validation token, the secure patient data may be released. The validation tokens for the patient and caregiver may be updated for each appointment, or may be updated every minute, day, month, etc. In some embodiments the validation tokens may be provided to the selected caregiver and the patient at the time of scheduling the appointment.

In another embodiment the determining whether the caregiver's authentication information satisfies the patient's verification information may include determining whether the geolocation of the caregiver is within a predetermined distance of the first patient's geolocation. For example, referring again to FIG. 7, the caregiver's verification information may include the location information of caregiver 240. The caregiver's verification information may be compared to the patient's verification information which includes the geolocation of the patient's service location 720. If the caregiver's location information is within a predetermined area, such as predetermined area 710 of the patient's service location 720, the central server or patient's computing device, may release the secure patient information.

In another embodiment, the determining whether the caregiver's authentication information satisfies the patient's verification information may include determining whether information on a network to which the caregiver device is connected is the same as networking data of the patient's verification information. In this regard, the patient's verification information may include network information, such as a networks name (i.e., service set identifier (SSID)), IP address, or other such information which identifies a network at the patient's service location. If the caregiver's verification information includes an indication that the caregiver is on the network at the patient's service location, the central server or patient's computing device, may release the secure patient information.

The patient or primary client contact may optionally control the release of the patient's secure patient information. In this regard, the patient's preferences may include an indication as to whether or not the patient wishes for his secure patient information to be released, as shown in block 607. In some embodiments the patient or primary client contact may also be able to control which portions of the secure patient information is released. For example, the patient may set his patient preferences to only allow for the release of current ailments and medications which are currently being taken. As such, the patient may block the selected caregiver from seeing all of his secure patient information. In some embodiments the patient or primary client contact may allow for the caregiver to access the secure patient information without caregiver authentication.

Figure 8:
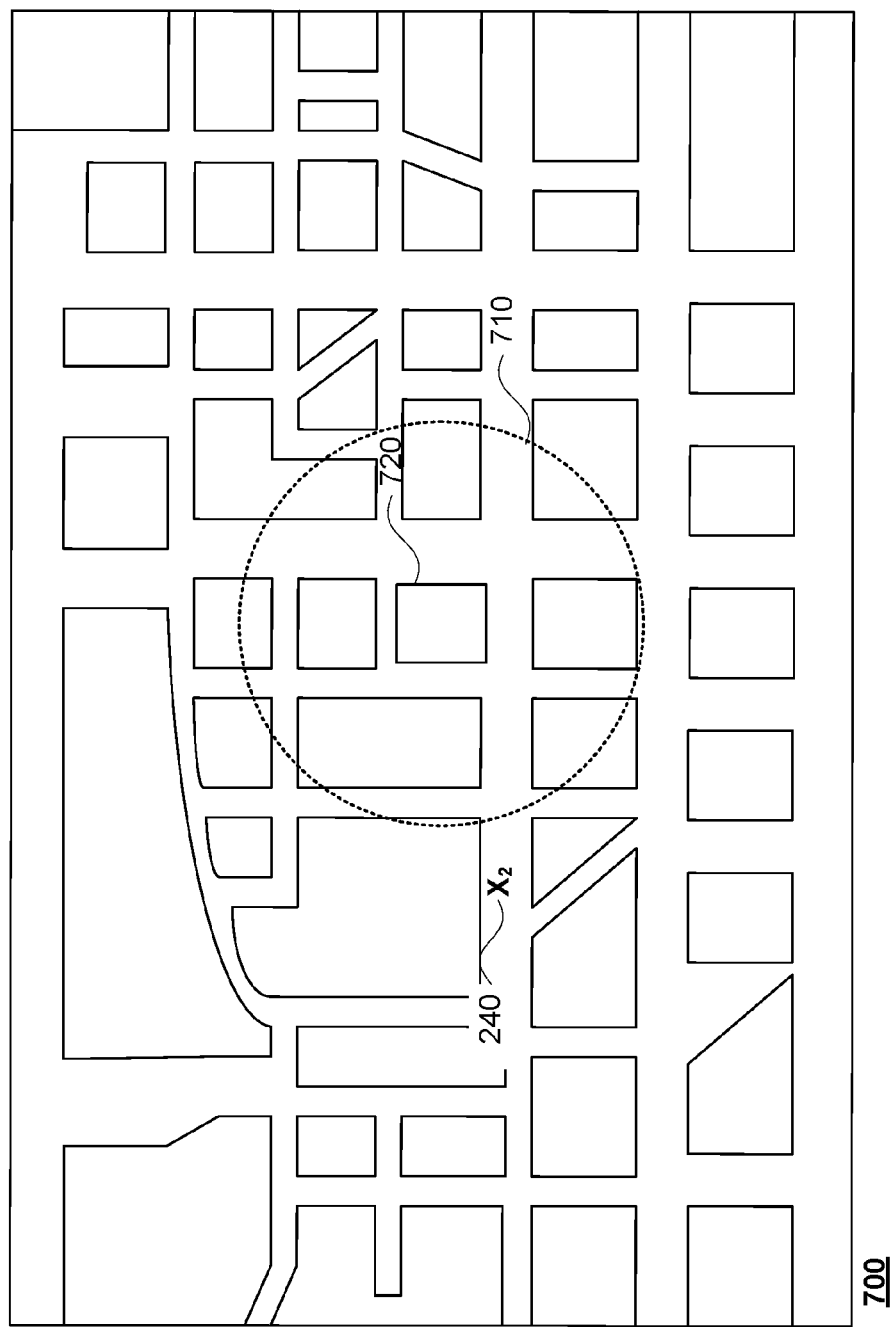
FIG. 8 is another example of caretaker tracking in accordance with aspects of the disclosure.

As shown in block 609, the caregiver's authentication information may be continually monitored to assure the patient's verification information is satisfied. In this regard, the caregiver's authentication information may be compared to the patient's verification information at a predetermined rate, such as every five minutes, or more or less, to assure that the scheduled caregiver still has permission to view the patient's verification information. The continual authentication process of block 609 may be performed using any of the foregoing authentication methods. For example, as shown in FIG. 8, the caregiver's verification information may include the location information of caregiver 240. The caregiver's verification information may be continually compared to the patient's verification information which includes the geolocation of the patient's service location 720. If the caregiver's location information is within a predetermined area, such as predetermined area 710 of the patient's service location 720, the central server or patient's computing device, may continue to allow the caregiver access to the secure patient information. Otherwise, when the caregiver's location information is outside of the predetermined area, such as caregiver location X2, the authentication may fail.

When the caregiver's authentication information fails to satisfy the patient's authentication information, the secure patient information may be removed, wiped, and/or deleted from the caregiver's device. In some embodiments the secure patient information may be automatically deleted from the caregiver's devices 140 after the scheduled appointment is completed, or after a predetermined time period. Further, the patient or primary contact may also trigger the removal of the secure patient information from the caregiver's device. In some embodiments the central server may query the caregiver device to assure that the secure patient information has been wiped.

Most of the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. As an example, the preceding operations do not have to be performed in the precise order described above. Rather, various steps can be handled in a different order, such as reversed, or simultaneously. Steps can also be omitted unless otherwise stated. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A computer implemented method for securely providing patient information, the method comprising:
    receiving, with one or more processors, verification information for a first patient, the verification information including a service location of the first patient, wherein the service location is a location where the first patient has a scheduled appointment with a caregiver, the verification information also including at least one of:
        i. a geolocation of service location; or
        ii. networking data of the service locations;
    storing, with the one or more processors, patient data for the first patient in association with the verification information;
    receiving, by the one or more processors, an authentication request to view the patient data, wherein the authentication request includes authentication information associated with a location of a device of the caregiver, and the authentication information includes a geolocation of the caregiver;
    determining, by the one or more processors, the authentication information satisfies the verification information, including determining whether the geolocation of the caregiver is within a predetermined distance of the geolocation of the service location;
    controlling release of the patient data to the caregiver device upon determining the authentication information satisfies the verification information;
    receiving updated authentication information from the caregiver;
    determining the updated authentication information is not within a predetermined distance of the service location; and
    controlling deletion of the patient data from the caregiver device, when the updated authentication information is not within the predetermined distance of the service location.

2. The method of claim 1, wherein prior to the release of the patient data, determining whether the verification information provides a grant of permission for the caregiver to access the patient data.

3. The method of claim 1, wherein the authentication information includes information on a network to which the caregiver device is connected, and determining whether the authentication information satisfies the verification information further comprises:
    determining whether the information on the network is the same as the networking data.

4. The method of claim 1, wherein the updated authentication information includes a geolocation of the caregiver; and
    determining the updated authentication information is not within a predetermined distance of the service location includes determining whether the geolocation of the caregiver is within a predetermined distance of the geolocation of the service location.

5. The method of claim 1, further comprising:
    receiving, with one or more processors, verification information for at least one additional patient, the at least one additional patient's verification information including data associated with second patient's service location; and
    storing, with the one or more processors, patient data for the at least one additional patient in association with the verification information of the at least one additional patient.

6. A system for securely providing patient information comprising:
    one or more computing devices; and
    memory storing instructions, the instructions executable by the one or more computing devices;
    wherein the instructions comprise:
        receiving, with the one or more computing devices, verification information for a first patient, the verification information including a service location of the first patient, wherein the service location is a location where the first patient has a scheduled appointment with a caregiver, the verification information also including at least one of:
            i. a geolocation of service location; or
            ii. networking data of the service locations;
        storing, with one or more computing devices, patient data for the first patient in association with the verification information;
        receiving, by the one or more computing devices, an authentication request to view the patient data, wherein the authentication request includes authentication information associated with a location of a device of the caregiver, and the authentication information includes a geolocation of the caregiver;
        determining, by the one or more computing devices, the authentication information satisfies the verification information;
        upon determining the authentication information satisfies the verification information, controlling release of the patient data to the caregiver device, including determining whether the geolocation of the caregiver is within a predetermined distance of the geolocation of the service location;
        receiving updated authentication information from the caregiver;
        determining the updated authentication information is not within a predetermined distance of the service location; and
        controlling deletion of the patient data from the caregiver device, when the updated authentication information is not within the predetermined distance of the service location.

7. The system of claim 6, wherein prior to the release of the patient data, determining whether the patient verification information provides a grant of permission for the caregiver to access the patient data.

8. The system of claim 6, wherein the authentication information includes information on a network to which the caregiver device is connected, and the determining whether the authentication information satisfies the verification information further comprises:
 determining whether the information on the network to which the caregiver device is connected is the same as the networking data of the verification information.

9. The system of claim 8, wherein the updated authentication information includes a geolocation of the caregiver; and
 determining the updated authentication information is not within a predetermined distance of the service location includes determining whether the geolocation of the caregiver is within a predetermined distance of the geolocation of the service location.

10. The system of claim 6, further comprising:
 receiving, with one or more processors, verification information for at least one additional patient, the at least one additional patient's verification information including data associated with second patient's service location; and
 storing, with the one or more processors, patient data for the at least one additional patient in association with the verification information of the at least one additional patient.

11. A non-transitory computer-readable medium storing instructions that, when executed by one or more processors, cause the one or more processors to perform the steps of:
 receiving verification information for a first patient, the verification information including a service location of the first, wherein the service location is a location where the first patient has a scheduled appointment with a caregiver, the verification information also including at least one of:
  i. a geolocation of service location; or
  ii. networking data of the service locations;
 storing patient data for the first patient in association with the verification information;
 receiving an authentication request to view the patient data, wherein the authentication request includes authentication information associated with a location of a device of the caregiver, and the authentication information includes a geolocation of the caregiver;
 determining the authentication information satisfies the verification information;
 upon determining the authentication information satisfies the verification information, controlling release of the patient data to the caregiver device, including determining whether the geolocation of the caregiver is within a predetermined distance of the geolocation of the service location;
 receiving updated authentication information from the caregiver;
 determining the updated authentication information is not within a predetermined distance of the service location; and
 controlling deletion of the patient data from the caregiver device, when the updated authentication information is not within the predetermined distance of the service location.

12. The non-transitory computer-readable medium, of claim 11, wherein prior to the release of the patient data, determining whether the verification information provides a grant of permission for the caregiver to access the patient data.

13. The non-transitory computer-readable medium of claim 11, wherein the authentication information includes information on a network to which the caregiver device is connected, and the determining whether the authentication information satisfies the verification information further comprises:
 determining whether the information on the network to which the caregiver device is connected is the same as the networking data of the verification information.

14. The non-transitory computer-readable medium of claim 11, further comprising:
 receiving, with one or more processors, verification information for at least one additional patient, the at least one additional patient's verification information including data associated with second patient's service location; and
 storing with the one or more processors, patient data for the at least one additional patient in association with the verification information of the at least one additional patient.

* * * * *